United States Patent
Li et al.

(10) Patent No.: US 11,079,389 B2
(45) Date of Patent: Aug. 3, 2021

(54) SYSTEM AND METHOD FOR IDENTIFICATION OF A SYNTHETIC CLASSIFER

(71) Applicant: ROCHE SEQUENCING SOLUTIONS, INC., Pleasanton, CA (US)

(72) Inventors: Hanying Li, Madison, WI (US); Ken Lo, Madison, WI (US); Jigar Patel, Verona, WI (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/891,385

(22) Filed: Jun. 3, 2020

(65) Prior Publication Data

US 2020/0309783 A1 Oct. 1, 2020

Related U.S. Application Data

(62) Division of application No. 15/720,969, filed on Sep. 29, 2017, now Pat. No. 10,697,973.

(60) Provisional application No. 62/404,084, filed on Oct. 4, 2016.

(51) Int. Cl.
| | |
|---|---|
| G01N 33/68 | (2006.01) |
| G01N 21/64 | (2006.01) |
| G01N 33/564 | (2006.01) |
| C40B 30/04 | (2006.01) |

(52) U.S. Cl.
CPC ..... *G01N 33/6803* (2013.01); *G01N 21/6428* (2013.01); *G01N 33/564* (2013.01); *G01N 33/68* (2013.01); *C40B 30/04* (2013.01); *G01N 2021/6439* (2013.01); *G01N 2333/001* (2013.01); *G01N 2333/005* (2013.01); *G01N 2570/00* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,709,558 B2 | 7/2017 | Johnston et al. | |
| 2005/0255491 A1* | 11/2005 | Lee et al. | G01N 33/6803 435/6.18 |
| 2008/0026485 A1* | 1/2008 | Hueber et al. | G01N 33/6854 436/507 |
| 2016/0003842 A1 | 1/2016 | Lee et al. | |
| 2017/0343541 A1 | 11/2017 | Johnston et al. | |

FOREIGN PATENT DOCUMENTS

| | | |
|---|---|---|
| JP | 2010-222300 A | 10/2010 |
| WO | WO-2007/123976 A2 | 11/2007 |
| WO | WO-2012/105838 A1 | 8/2012 |
| WO | WO-2015/059168 A1 | 4/2015 |
| WO | WO-2016/040703 | 3/2016 |

OTHER PUBLICATIONS

Hansson et al., "Validation of a multiplex chip-based assay for the detection of autoantibodies against citrullinated peptides," Arthritis Res. Ther. 2012, 14:R201. (Year: 2012).*
Notification of Reasons for Rejection in JP Patent Application No. 2019-538718 dated Jun. 1, 2020 (with English translation) (17 pages).
Araujo et al., "Improved Serological Detection of Rheumatoid Arthritis: A Highly Antigenic Mimotope of Carbonic Anydrdase III selected In a Murine Model by Phage Display", Jun. 23, 2015, BioMed Central, vol. 17, Issue 168, pp. 1-13.
Cao et al., "Two Classifier Based on Serum Peptide Pattern for Prediction Pattersn of HBV-Induced Liver Cirrhosis Using MALDI-TOF MS", Jan. 1, 2013, Biomed. Research International, vol. 2013, pp. 1-7.
Gasparini et al., "MicroRNA Classifiers are Powerful Diagnostics/Prognostic Tools in ALK-, EGFR-, and KRAS-drive Lung Cancers", Dec. 1, 2015, PNAS, vol. 112, No. 48, pp. 14924-14929.
Gearhart et al., "Selection of a Potential Diagnostic Biomarker for HIV Infection from a Random Library of Non-Biological Synthetic Peptoid Oligomers", May 12, 2016, Journal of Immunological Methods, vol. 435, No. 12, pp. 85-89.
Good et al., "Naturally Occurring Human Urinary Petides for Use in Diagnosis of Chronic Kidney Disease", Molecular and Cellular Proteomics, Jul. 8, 2010, vol. 9, Issue 11, pp. 2424-2437.
Hansson, et al., "Validation of a multiplex chip-based assay for the detection of autoantibodies against citrullinated peptides," Arthritis Res. Ther., 14:R201 (2012).
International Preliminary Report on Patentability in International Patent Application No. PCT/EP2017/074683 dated Apr. 9, 2019 (8 pages).
International Search Report and Written Opinion in International Patent Application No. PCT/EP2017/074683 dated Jan. 30, 2018 (13 pages).
Jankowski et al., "Body Fluid Peptide and Protein Signatures in Diabetic Kidney Diseases", Jul. 24, 2015, Nephrology Dialysis Transplantation, vol. 30, No. 4, pp. iv43-iv53.

(Continued)

*Primary Examiner* — Kaijiang Zhang
(74) *Attorney, Agent, or Firm* — Foley & Lardner LLP

(57) ABSTRACT

The present invention provides a method for identifying a synthetic classifier including contacting at least a first and second samples derived from different groups of a cohort with a first plurality of peptides. The first plurality of peptides includes a first subset of peptides defining at least one naturally occurring amino acid sequence, and a second subset of peptides defining a plurality of variants of the first subset of peptides. The plurality of variants includes, for each one of the first subset of peptides, a variant peptide having at least one of a substitution, a deletion, an insertion, an extension, and a modification. The method further includes selecting at least one of the plurality of variants from the second subset of peptides, and defining a synthetic classifier including the at least one of the plurality of variants that distinguishes between samples derived from the first and second cohorts.

9 Claims, 7 Drawing Sheets

Specification includes a Sequence Listing.

(56) References Cited

OTHER PUBLICATIONS

Mewar et al., "Antiferritin Antibodies Discovered by Phage Display Expression Cloning are Associated with Radiographic Damage in Rheumatoid Arthritis", Arthritis and Rheumatism, Dec. 2005, vol. 52, Issue 12, pp. 3868-3872.
Non-Final Office Action in U.S. Appl. No. 15/720,969 dated Oct. 1, 2019 (15 pages).
Notice of Allowance in U.S. Appl. No. 15/720,969 dated Mar. 6, 2020 (7 pages ).
Reddy et al., "Identification of Candiate IgG Biomarkers for Alzheimer's Disease via Combinatorial Library Screening", Nov. 19, 2010, Cell, vol. 144, No. 1, pp. 132-142.
Stalmach et al., "Identification of Urinary Peptide Biomarkers Associated with Rheumatoid Arthritis", Aug. 1, 2014, Plos One, vol. 9, No. 1, pp. 1-9.
Strimbu et al., "What are Biomarkers?", Current Opinion in HIV and AIDS, Nov. 2010, vol. 5, Issue 6, pp. 463-466.
Trier et al., "Application of Synthetic Peptides for Detection of Anti-Citrullinated Peptide Antibodies", Jan. 12, 2016, Peptides, vol. 76, pp. 87-95.

\* cited by examiner

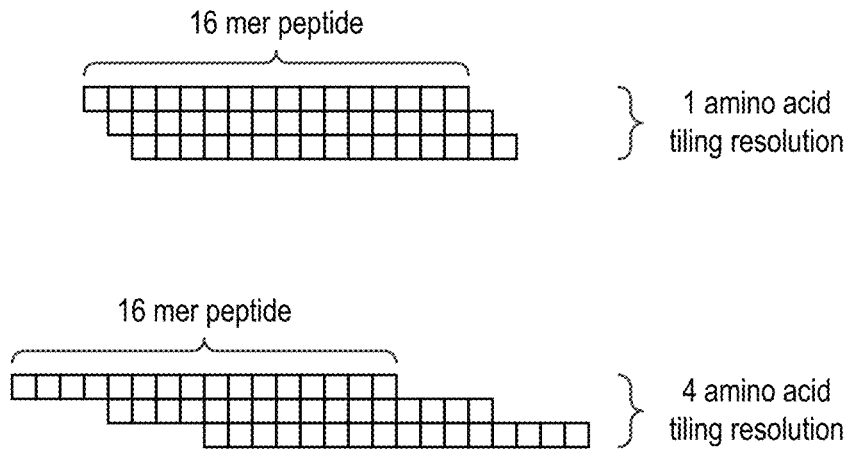

Protein Sequence A: EGVKLTALNDSSLDLSMDSDNSMSV...
(1 amino-acid tiling resolution)

|  | Position | Sequence |
| --- | --- | --- |
| Peptide 1 | 1 | EGVKLTALNDSSLDLS |
| Peptide 2 | 2 | GVKLTALNDSSLDLSM |
| Peptide 3 | 3 | VKLTALNDSSLDLSMD |
| Peptide 4 | 4 | KLTALNDSSLDLSMDS |
| Peptide 5 | 5 | LTALNDSSLDLSMDSD |
| Peptide 6 | 6 | TALNDSSLDLSMDSDN |
| Peptide 7 | 7 | ALNDSSLDLSMDSDNS |
| Peptide 8 | 8 | LNDSSLDLSMDSDNSM |
| Peptide 9 | 9 | NDSSLDLSMDSDNSMS |
| Peptide 10 | 10 | DSSLDLSMDSDNSMSV |
| Peptide X | n | ---------------- |

FIG. 2

SEQUENCE LISTING

```
<160> NUMBER OF SEQ ID NOS: 1

<210> SEQ ID NO 1
<211> LENGTH: 25
<212> TYPE: PRT
<213> ORGANISM: Homo sapiens

<400> SEQUENCE: 1

Glu Gly Val Lys Leu Thr Ala Leu Asn Asp Ser Ser Leu Asp Leu Ser
1               5                   10                  15

Met Asp Ser Asp Asn Ser Met Ser Val
            20                  25
```

SYSTEM AND METHOD FOR IDENTIFICATION OF A SYNTHETIC CLASSIFER

CROSS-REFERENCE TO RELATED APPLICATIONS

This application is a divisional of U.S. patent application Ser. No. 15/720,969, filed on Sep. 29, 2017, which claims the benefit of and priority to U.S. Provisional Patent Application No. 62/404,084 filed on Oct. 4, 2016 and entitled, "System and Method for Identification of a Synthetic Classifier," the contents of which are incorporated herein by references in their entireties.

STATEMENT REGARDING FEDERALLY SPONSORED RESEARCH

Not applicable.

BACKGROUND

The disclosure relates, in general, to the design and selection of synthetic peptides for interrogating biomarkers and, more particularly, to a system and method for identifying and implementing a synthetic classifier including one or more variant peptides for diagnostic and predictive applications.

Biomarkers are naturally occurring, biological elements (e.g., nucleic acids, proteins, small molecules, and the like) that are generally detected in the blood, urine, or another fluid of a subject. Such biomarkers may form the basis of a diagnostic or prognostic classifier. One example of a biomarker includes microRNAs (miRNAs), which can have unique profiles in a subject that can be indicative of the presence or absence of a given disease and can further be predictive of disease progression. In the context of non-small cell lung cancer (NSCLC), Gasparini et al. developed a diagnostic classifier that demonstrated the expression signatures of various miRNAs could be used to classify NSCLCs as ALK-translocated, mutant EGFR, or mutant KRAS versus mutation-free (Gasparini et al. 2015, *microRNA classifiers are powerful diagnostic/prognostic tools in ALK-, EGFR-, and KRAS-driven lung cancers.* PNAS, vol. 112, no. 48, pp. 14924-14929). Gasparini et al. further identified a prognostic miRNA-based classifier to predict overall survival.

One potential drawback of the approach taken by Gasparini et al. and others, is that a given classifier is limited to those biomarkers derived from a given subject that are naturally occurring (wild-type or mutant). Moreover, development of such biomarker-based classifiers can be time-consuming both in terms of the length of time it takes to identify and validate the classifier as well as the extent of the labor required to process samples, design experiments, analyze date, and the like.

Accordingly, there is a need for improved processes and systems for the development of new classifiers for both diagnostic and prognostic applications.

SUMMARY

The present invention overcomes the aforementioned drawbacks by providing a system and method for identification of a synthetic classifier.

In accordance with one embodiment of the present disclosure, a method for identifying a synthetic classifier includes contacting at least a first sample and a second sample with a first plurality of peptides, the first sample derived from a first group of a cohort, the second sample derived from a second group of the cohort, the first group being different from the second group, and at least a portion of the first plurality of peptides defining at least one naturally occurring amino acid sequence. The method further includes selecting a first subset of peptides from the first plurality of peptides, and contacting at least the first sample and the second sample with a second plurality of peptides, at least a portion of the second plurality of peptides defining the sequences of the first subset of peptides and a plurality of variant peptides of the first subset of peptides, the plurality of variant peptides including for each one of the first subset of peptides, a variant peptide having at least one of a substitution, a deletion, an insertion, an extension, and a modification. Examples of a substitution, a deletion, an insertion, an extension, and a modification with respect to the preparation of variant or modified peptides is described at least in U.S. patent application Ser. No. 15/233,543 to Bannen et al. The method further includes selecting a second subset of peptides from the second plurality of peptides, the second subset of peptides including at least one of the plurality of variant peptides, the second subset of peptides at least partially defining a synthetic classifier, the synthetic classifier distinguishing between a sample derived from the first group and a sample derived from the second group.

In accordance with another embodiment of the present disclosure, a method for identifying a synthetic classifier includes contacting at least a first sample and a second sample with a first plurality of peptides, the first sample derived from a first group of a cohort, the second sample derived from a second group of the cohort, the first group being different from the second group, and the first plurality of peptides including: i) a first subset of peptides defining at least one naturally occurring protein sequence, and ii) a second subset of peptides defining a plurality of variant peptides of the first subset of peptides, the plurality of variant peptides including for each one of the first subset of peptides, a variant peptide having at least one of a substitution, a deletion, an insertion, an extension, and a modification. The method further includes selecting at least one of the plurality of variant peptides from the second subset of peptides, and defining a synthetic classifier including the at least one of the plurality of variant peptides, the synthetic classifier distinguishing between a sample derived from the first group and a sample derived from the second group.

In accordance with another embodiment of the present disclosure a method for identifying a synthetic classifier includes a step of contacting at least a first sample and a second sample with a first plurality of peptides. The first sample is derived from a first group of a cohort, and the second sample derived from a second group of the cohort. The first group is different from the second group, and at least a portion of the first plurality of peptides define at least one naturally occurring amino acid sequence. The method further includes a step of selecting a first subset of peptides from the first plurality of peptides, and contacting at least the first sample and the second sample with a second plurality of peptides. At least a portion of the second plurality of peptides includes a plurality of variant peptides of the first subset of peptides, each of the plurality of variant peptides having at least one of a substitution, a deletion, an insertion, an extension, and a modification relative to a corresponding one of the first subset of peptides. The method further includes selecting a second subset of peptides from the second plurality of peptides. The second subset of peptides includes at least one of the plurality of variant peptides. The second subset of peptides at least partially defines a synthetic classifier that distinguishes between a sample derived from the first group and a sample derived from the second group.

In one aspect of the method, the first plurality of peptides represent at least about 90% of a target proteome, the target proteome selected from a virus and an organism.

In another aspect of the method, the synthetic classifier distinguishes between the sample derived from the first group and the sample derived from the second group with at least one of a greater sensitivity and a greater specificity than a natural classifier consisting of peptides selected from the first subset of peptides.

In another aspect of the method, each of the peptides in the first plurality of peptides and the second plurality of peptides is between about 12 amino acids and about 16 amino acids in length.

In another aspect of the method, the peptides in the first plurality of peptides are tiled at between 1 amino acid and 4 amino acids.

In another aspect of the method, the synthetic classifier is one of a diagnostic classifier and a prognostic classifier.

In another aspect of the method, each one of the variant peptides corresponds to a naturally occurring peptide, and each one of the variant peptides has a sequence that differs from the corresponding naturally occurring peptides sequence with respect to at least one amino acid position.

In another aspect of the method, the at least one of the plurality of variant peptides in the synthetic classifier is a synthetic peptide having a sequence that differs from any naturally occurring peptide sequence associated with either of the first group and the second group.

In another aspect, the method further includes detecting a first signal output characteristic of an interaction of each of the first sample and the second sample with the first plurality of peptides, selecting the first subset of peptides based on the first signal output, detecting a second signal output characteristic of an interaction of each of the first sample and the second sample with the second plurality of peptides, and selecting the second subset of peptides based on the second signal output. In one aspect, the first signal output is a fluorescence intensity obtained through fluorophore excitation-emission, the fluorescence intensity reflecting at least one of i) an abundance of a component of one of the first sample and the second sample associated with the first plurality of peptides, and ii) a binding affinity of the component of one of the first sample and the second sample to the first plurality of peptides. The second signal output is a fluorescence intensity obtained through fluorophore excitation-emission, the fluorescence intensity reflecting at least one of i) an abundance of a component of one of the first sample and the second sample associated with the second plurality of peptides, and ii) a binding affinity of the component of one of the first sample and the second sample to the second plurality of peptides.

In accordance with another embodiment of the present disclosure, a method for identifying a synthetic classifier includes contacting at least a first sample and a second sample with a first plurality of peptides, the first sample derived from a first group of a cohort, the second sample derived from a second group of the cohort, and the first group being different from the second group. The first plurality of peptides includes a first subset of peptides defining at least one naturally occurring amino acid sequence, and a second subset of peptides defining a plurality of variant peptides of the first subset of peptides. The plurality of variant peptides includes for each one of the first subset of peptides, a variant peptide having at least one of a substitution, a deletion, an insertion, an extension, and a modification relative to a corresponding one of the first subset of peptides. The method further includes selecting at least one of the plurality of variant peptides from the second subset of peptides, and defining a synthetic classifier including the at least one of the plurality of variant peptides, the synthetic classifier distinguishing between a sample derived from the first group and a sample derived from the second group.

In one aspect of the method, at least a portion of the first plurality of peptides represents at least about 90% of a target proteome, the target proteome selected from a virus and an organism.

In another aspect of the method, the synthetic classifier distinguishes between the sample derived from the first group and the sample derived from the second group with at least one of a greater sensitivity and a greater specificity than a natural classifier consisting of peptides selected from the first subset of peptides.

In another aspect of the method, each of the peptides in the first plurality of peptides is between about 12 amino acids and about 16 amino acids in length.

In another aspect of the method, the peptides in the first plurality of peptides are tiled at between 1 amino acid and 4 amino acids.

In another aspect of the method, each one of the variant peptides corresponds to a naturally occurring peptide, and each one of the variant peptides has a sequence that differs from the corresponding naturally occurring peptides sequence with respect to at least one amino acid position.

In another aspect of the method, the at least one of the plurality of variant peptides in the synthetic classifier is a synthetic peptide having a sequence that differs from any naturally occurring peptide sequence associated with either of the first group and the second group.

In another aspect, the method further includes detecting a first signal output characteristic of an interaction of each of the first sample and the second sample with the first plurality of peptides, and selecting the first subset of peptides based on the first signal output. In one aspect, the first signal output is a fluorescence intensity obtained through fluorophore excitation-emission, the fluorescence intensity reflecting at least one of i) an abundance of a component of one of the first sample and the second sample associated with the first plurality of peptides, and ii) a binding affinity of the component of one of the first sample and the second sample to the first plurality of peptides.

In accordance with another embodiment of the present disclosure, a composition includes a plurality of synthetic peptides. Each of the synthetic peptides have at least one of a substitution, a deletion, an insertion, an extension, and a modification relative to a corresponding peptide defining at least one naturally occurring amino acid sequence. The synthetic peptides at least partially define a synthetic classifier. The synthetic classifier distinguishes between a sample derived from a first group of a cohort and a sample derived from a second group of the cohort.

In accordance with another embodiment of the present disclosure, a kit for classifying a sample includes a plurality of synthetic peptides. Each of the synthetic peptides have at least one of a substitution, a deletion, an insertion, an extension, and a modification relative to a corresponding peptide defining at least one naturally occurring amino acid sequence. The synthetic peptides at least partially define a synthetic classifier. The synthetic classifier distinguishes between a sample derived from a first group of a cohort and a sample derived from a second group of the cohort.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2 is a schematic illustration of 16-mer peptides tiled at either 1 amino acid resolution or 4 amino acid resolution, including a table illustrating tiling of a portion of an example protein sequence EGVKLTALNDSSLDLSMDSDNSMSV (SEQ ID NO:1) represented with 16-mer peptides tiled at 1 amino acid resolution.

FIG. 4A is a set of two scatter plots showing the $\log_2$ signal response of different serum samples in the presence of one of two pairs of wild-type/derivative peptides. The signal for the wild-type peptide of each pair of peptides is shown on the horizontal axis and the signal for the corresponding derivative peptide (wild-type peptide having arginine and lysine substituted with citrulline and homocitrulline, respectively) is shown on the vertical axis for each of 30 serum samples from three different sample groups within a cohort of subjects. Wild-type/derivative peptide pairs were identified from an array of peptides representing the entirety of the human proteome. FIG. 4B is a discrimination plot generated from the data illustrated in FIG. 4A. By combing the data from the individual plots, the two peptides were able to generally distinguish between the control group (empty squares), the DMARDS/responders group (empty circles) and non-responders group (filled circles). In both FIGS. 4A and 4B, each data point represents one serum sample; dashed circles indicate general colocalization of data points from like sample groups.

DETAILED DESCRIPTION

I. Definitions

Figure 1:
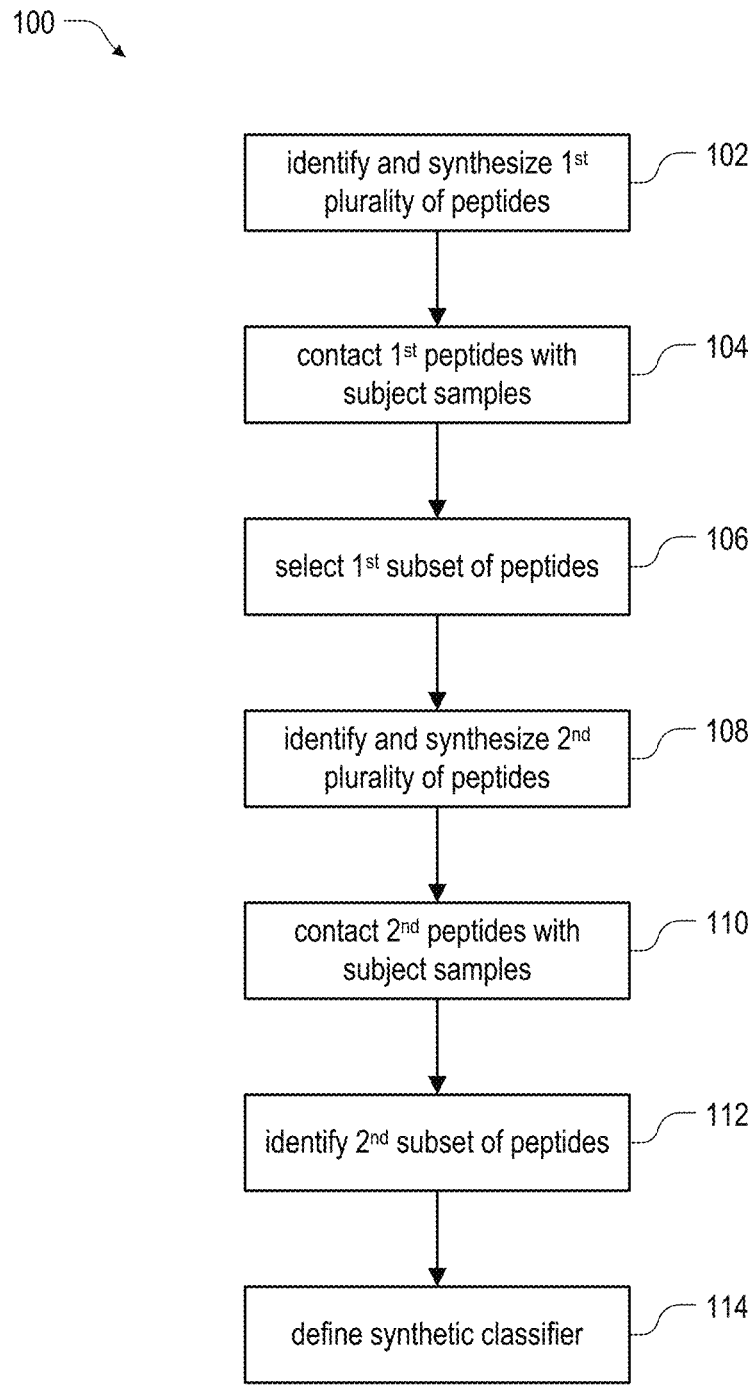
FIG. 1 is an example of a method of for identifying a synthetic classifier according to the present disclosure.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level, and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biological Sample: As used herein, the term "biological sample" typically refers to a sample obtained or derived from a biological source (e.g., a tissue or organism or cell culture) of interest, as described herein. In some embodiments, a source of interest comprises or consists of an organism, such as an animal or human. In some embodiments, a biological sample is comprises or consists of biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample is comprises or consists of cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Comprising: A composition or method described herein as "comprising" one or more named elements or steps is open-ended, meaning that the named elements or steps are essential, but other elements or steps may be added within the scope of the composition or method. It is to be understood that composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Designed: As used herein, the term "designed" refers to an agent (i) whose structure is or was selected by the hand of man; (ii) that is produced by a process requiring the hand of man; and/or (iii) that is distinct from natural substances and other known agents.

Determine: Those of ordinary skill in the art, reading the present specification, will appreciate that "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Sample: As used herein, the term "sample" refers to a substance that is or contains a composition of interest for qualitative and or quantitative assessment. In some embodiments, a sample is a biological sample (i.e., comes from a living thing (e.g., cell or organism). In some embodiments, a sample is from a geological, aquatic, astronomical, or agricultural source. In some embodiments, a source of interest comprises or consists of an organism, such as an animal or human. In some embodiments, a sample for forensic analysis is or comprises biological tissue, biological fluid, organic or non-organic matter such as, e.g., clothing, dirt, plastic, water. In some embodiments, an agricultural sample, comprises or consists of organic matter such as leaves, petals, bark, wood, seeds, plants, fruit, etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Synthetic: As used herein, the word "synthetic" means produced by the hand of man, and therefore in a form that does not exist in nature, either because it has a structure that does not exist in nature, or because it is either associated with one or more other components, with which it is not associated in nature, or not associated with one or more other components with which it is associated in nature.

Synthetic Peptide: As used herein, the term "synthetic peptide" refers to a peptide that differs from a naturally occurring peptide at one or more amino acid positions. In one aspect, a synthetic peptide can be differentiated from both a wild-type peptide and a mutant or other naturally occurring peptide. For example, a wild-type peptide can consist of a peptide sequence defining at least a portion of a wild-type protein sequence. In some cases, the wild-type protein may be known to occur naturally in a mutant form. For example, in certain autoimmune diseases, selected proteins are observed to include one or more citrulline residues in place of arginine residues. Notably, this citrullination is known to occur in nature. In this case, an example mutant peptide can consist of a peptide sequence defining at least a portion of the citrullinated protein sequence. However, the mutant peptide including the one or more citrulline residues can still be considered to be a naturally occurring peptide. By contrast, a synthetic peptide will differ from a wild-type peptide, a mutant peptide, or another naturally occurring peptide sequence defining at least a portion of a naturally occurring protein sequence. In one example, a synthetic peptide can include one or more amino acid substitutions, deletions, insertions, other like modifications, or a combination thereof, where the aforementioned modifications are not observed in a naturally occurring form of the protein sequence to which the peptide corresponds.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, a variant may also have one or more functional defects and/or may otherwise be considered a "mutant". In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

II. Detailed Description of Certain Embodiments

As also discussed above, in various situations it may be useful to provide a method for accurately diagnosing a subject for a particular condition, disease, or the like. Depending on the nature of the diagnostic, the method or test can enable early detection, potentially resulting in improved opportunities to plan for treatment and the like. However, a given affliction may be difficult to accurately diagnose, especially early on, when detectable symptoms are restricted to changes at the molecular level (e.g., genomic mutations, protein aggregation, changes in expression levels of nucleic acids or proteins, and the like) that may not have manifested in more readily detectable ways. For example, Alzheimer's disease (AD) is a chronic neurodegenerative disease that can include such outward manifestations as memory loss, confusion, and decreased or poor judgment. However, while the cause of AD is poorly understood, biochemical changes including protein misfolding are hypothesized to contribute to the progression of the disease. Accordingly, examination of brain tissue is presently needed for a more definite diagnosis. That is, diagnosis of a disease, such as AD, may benefit from a diagnostic that focuses on biomarkers such as peptides, proteins, or nucleic acids as opposed to behavioral characteristics or other outward manifestations that can be subjective or difficult to detect early in the progression of the condition.

In another example, it may be useful to provide a method for accurately forecasting the probable course of a disease or determining whether a subject may respond to a given course of treatment (i.e., a prognostic or predictive method). More than one treatment method is often available for use; however, if no predictive test is available to indicate which treatment or treatments will be effective, it may be necessary to rely on trial and error, attempting multiple different treatments either alone or in combination to determine which treatments will be effective. Ultimately, in the absence of either or both of a diagnostic and prognostic method or test, several challenges may arise in the diagnosis and treatment of a subject.

These and other challenges may be overcome with a system and method for the design and implementation of a synthetic classifier. In one aspect, a classifier can be implemented to solve the problem of categorizing a subject within population of subjects. For example, a classifier may assign a subject (or observation about that subject) to a particular category or sub-population based on a training set of data containing information about one or more different subjects (or observations) within the population. An example would be assigning a diagnosis to a given subject as determined by observed characteristics of the subject.

The present disclosure is, at least in part, based on the surprising discovery that a set of one or more synthetic peptides (i.e., non-naturally occurring variants of known peptide sequences) can be used to prepare a one or both of a diagnostic and a prognostic classifier for categorizing an observation or aspect of a group of subjects. For example, an observation about the interaction of the synthetic peptides with a serum sample collected from the subject can be used to diagnose the subject for a given condition, predict which treatment or treatments may be effective for the subject, the like, and combinations thereof. Moreover, the present disclosure provides for general methods of identifying and implementing a synthetic classifier for almost any situation where an interaction can be detected between one or more synthetic peptides and a biomarker derived from or present within a subject.

In one aspect, a synthetic classifier according to the present disclosure can include synthetic peptides that are differentiable from a traditional classifier for querying a biomarker. A biomarker can be defined as a naturally occurring, biological element (e.g., a nucleic acid, a protein, a small molecule, an antibody, or the like) that can be detected in the blood, urine, or another fluid of a subject. In one aspect, the biomarker may be produced by a foreign (non-native) or mutant (native) element in the subject (e.g., a tumor, a virus, a parasite, or the like) or in response to the presence of the native or non-native element. In general, querying of biomarkers can allow for early detection of a condition, confirmation of a diagnosis, predicting an outcome or making a prognosis, monitoring treatment response, and the like. Whereas some classifiers can include one or more elements for querying biomarkers such as normal or mutant peptides or proteins, the synthetic peptides of the present disclosure cannot be properly equated to these normal or mutant peptides or proteins. In one aspect, the synthetic peptides of the present disclosure may be variants of normal (wild-type) or mutant versions of peptides or proteins that may exist in a given subject or may be associated with a given condition. While the native peptides (wild-type or mutant) may be predicted to be useful for querying a biomarkers as they may be observed to interact with those biomarker in nature, the synthetic peptides of the present disclosure are non-naturally occurring, designed sequences that are absent in the curated proteome. However, these synthetic peptides may contribute to a more sensitive and/or specific classifier for querying those same biomarkers. Without being limited by any particular theory, it is hypothesized that the synthetic peptides of the present disclosure may adopt a conformation that it is better suited to interact with or be bound by a portion of a serum antibody or another biomarker relative to naturally occurring peptide sequences. Importantly, the synthetic peptides of the present disclosure can be capable of detecting or otherwise interacting with one or more biomarkers derived from a subject as the basis of a diagnostic or prognostic/predictive synthetic classifier.

In one aspect, the present disclosure leverages the surprising discovery that a synthetic or variant peptide sequence can be used to provide a classifier, as one would not necessarily expect to find non-naturally occurring peptides that can be used as a classifier to discriminate between naturally occurring biomarkers. In light of this result, the present disclosure provides for systems and methods to design peptide-based probes for detection of biomarkers that may be useful in one or more of predictive, prognostic, diagnostic, pharmacodynamic, and/or efficacy-response applications. As further defined herein, a biomarker is a measurable substance in an organism whose presence is indicative of some phenomenon such as disease, infection, or environmental exposure. Methods according to the present disclosure for detection of one or more biomarkers include i) systematic screening of known peptide targets as an initial step for candidate peptide identification, and ii) subsequent derivatization of candidates that can include systematic mutation of candidates with both natural and non-natural amino acids, cyclization of candidates and their mutant counterparts, or a combination thereof to provide a plurality of synthetic variants of the candidate peptides. Derivatization is based on the ability to distinguish between sub-groups of biomarker populations (e.g., drug responders vs. non-responders, or diseased vs. control/healthy populations) in a disease area.

In one aspect, the present disclosure overcomes the challenge of having to rely solely on screening to identify peptide candidates and using them as probes to query biomarkers. Existing solutions rely on methods such as phage or mRNA display for natural amino acids substitution. As for non-natural amino acids such as citrulline and homocitrulline, work is ongoing to overcome the challenge of incorporating non-natural amino acids into various display technologies (e.g., mRNA display, phage display, etc.) via genetic code expansion or genetic code reprogramming. By contrast, embodiments of the present disclosure involve systematically mutating these peptide candidates to find variant peptide sequences (i.e., synthetic peptides) that perform better than the original, naturally occurring candidate peptides as probes for querying biomarkers. These variant peptide sequences are unlikely to be found in the human proteome (natural vs. non-natural), and are at least unknown (i.e., non-naturally occurring) variants of the portions of the proteins from which they are derived. In one aspect, the synthetic peptides of the present disclosure can be implemented in detection schemes for the accurate diagnosis of a subject with a given condition as well as for informing which treatments may be effective for a given subject.

Turning to FIG. 1, an embodiment of a method 100 for identifying a synthetic classifier includes a step 102 of identifying and synthesizing a first plurality of peptides. At least a portion of the first plurality of peptides can define at least one naturally occurring amino acid sequence. For example, the peptides can be tiled at 1 amino acid resolution (see FIG. 2) along the length of an entire partial or full length protein sequence of interest. In some embodiments, the peptides can have amino acid sequences that collectively represent the entire human proteome or another proteome of interest. A next step 104 of the method 100 includes contacting at least a first sample and a second sample with a first plurality of peptides. The first sample is derived from a first group of a cohort, and the second sample derived from a second group of the cohort. The first group is different from the second group. The cohort is generally a group of subjects with a common defining characteristic. For example, the cohort can be a group of subjects, where a portion of the subjects have been diagnosed with a particular condition or disease. More particularly, the first group within the cohort can be a group of healthy (control) subjects and the second group within the cohort can be a group of subjects known to have a particular condition, disease, diagnosis, or the like.

Notably, samples can be derived from two or more groups within a cohort. As described in the Examples below, in some embodiments, a cohort can include three or more groups. Example groups can include at least a control or healthy subject group, a group of subjects diagnosed with a particular condition where the subjects responded to a particular treatment, and a group of subjects diagnosed with the same particular condition where the subjects did not respond to the particular treatment. Moreover, more than a single sample may be tested from each of the groups within the cohort. For example, at least 2, 3, 4, 5, 6, 7, 8, 9, 10, 15, 20, 30, 50, 100, 1,000, 10,000, or more samples can be obtained for each group within a cohort. Each of the samples from a selected group of the cohort can be contacted individually or in combination with one or more peptides as described below. In one aspect, a sample can be a blood sample, a serum sample, a buccal swab, a urine sample, a stool sample, a tissue sample, the like, or combinations thereof. The single sample will generally be collected from an individual subject. However, in some embodiments, it may be useful to pool one or more samples to provide a single, combined sample.

A next step 106 of the method 100 includes selecting a first subset of peptides from the first plurality of peptides. The first subset of peptides can be candidate peptides that can at least partially classify the first and second samples from the first and second groups. A next step 108 of the method 100 includes identifying and synthesizing a second plurality of peptides. At least a portion of the second plurality of peptides can define the sequences of the first subset of peptides and a plurality of variant peptides of the first subset of peptides. For example, the plurality of variant peptides can include, for each one of the first subset of peptides, a variant peptide having at least one of a substitution, a deletion, an insertion, an extension, and a modification. In one aspect, the plurality of variant peptides can include one or more synthetic peptides as defined herein.

A next step 110 of the method 100 can include contacting at least the first sample and the second sample (or samples comparable thereto) with a second plurality of peptides. Thereafter, a next step 112 of the method 100 can include identifying or otherwise selecting a second subset of peptides from the second plurality of peptides. The second subset of peptides can include at least one of the plurality of variant peptides. In a next step 114 of the method 100, a synthetic classifier can be defined including at least one of the second subset of peptides. The synthetic classifier can distinguish between a sample derived from the first group and a sample derived from the second group. Moreover, the synthetic classifier can include one or more synthetic peptides identified according to the method 100.

Notably, the embodiments of the method 100 according to the present disclosure can include one or more additional steps or omit one or more of the illustrated steps of the method 100. For example, it may be possible to identify a subset of peptides from which a plurality of variant peptides can be prepared without performing the initial steps of the method 100. That is, it may be possible to omit the steps of identifying and synthesizing a first plurality of peptides, contacting the first plurality of peptides with the subject samples, and selecting the first subset of peptides based on the outcome of the first and second illustrated steps of the method 100 of identifying and contacting. Accordingly, the method 100 can begin with a step of identifying and synthesizing the second plurality of peptides. In general, the method 100 can be modified in any suitable way that still enables the outcome of defining a classifier, whether the resulting classifier is synthetic or otherwise. Yet other variations of the method 100 that fall within the scope of the present disclosure will be apparent from the additional examples and description included herein.

EXAMPLES

The following Examples are meant to be illustrative and are not intended to be limiting in any way.

Example 1

Rheumatoid arthritis (RA) is systemic inflammatory disease which manifests itself in multiple joints (e.g., more than five joint) of the body. The inflammatory process primarily affects the lining of the joints (synovial membrane), but can also affect other organs. The inflamed synovium leads to erosions of the cartilage and bone and sometimes joint deformity. As it is an autoimmune disease, autoantibodies such as rheumatoid factor (RF) are often present in the serum samples isolated from RA patients. In the late 1990s, citrullination of arginine and more recently, homo-citrullination of lysine have been identified as antigenic determinants of autoantibodies isolated from serum of RA patients (see also Prujin et al., 2015. *Citrullination and carbamylation in the pathophysiology of rheumatoid arthritis*, Front Immunol. vol. 6, iss. 192). Typical first-line treatment of RA includes the use of disease-modifying antirheumatic drugs (DMARDS).

Profiling of antibodies, autoantibodies, or a combination thereof using peptide arrays has been described previously (see, e.g., U.S. Pat. Pub. No. 2015/0185216 to Albert et al.); however, the citrullinated and homo-citrullinated epitopes of RA patients' serum samples have not been fully characterized. To this end, thirty (30) serum samples were obtained from subjects in each of three different groups of a cohort for a total of ninety (90) serum samples from the cohort of subjects. The three different thirty subject groups (subpopulations) of the cohort included i) a control or healthy donor group (i.e., subjects diagnosed as being negative for RA), ii) a responder or DMARDS group of RA patients who responded to first line treatment (i.e., RA patients that responded to treatment with DMARDS such as methotrexate), and iii) a non-responder group of RA patients that had failed first line treatment and at least 1 biologic (e.g., Anti-TNF-α, anti-CD20, anti-IL-6, IL-1 receptor antagonist, T-cell costimulatory blocker, or the like).

An initial screening of the ninety serum samples was performed with a first array design whose content included peptides representing 52 proteins identified to have been citrullinated from synovial fluid of 2 RA patients using mass spectrometry (Van Beers et al., 2013. *The rheumatoid arthritis synovial fluid citrullinome reveals novel citrullinated epitopes in apolioprotein E, myeloid nuclear differentiation antigen, and β-actin*. Arthritis & Rheumatism. 65(469-80). The proteins were tiled with overlapping 12-mer peptides at 1 amino-acid tiling resolution (see FIG. 2 for an example of 1 amino-acid tiling resolution). For all peptides containing amino acids arginine and lysine, a derivative peptide was also synthesized (i.e., included in the first array design) by substituting citrulline for arginine and homocitrulline for lysine. Notably, while selected arginine and lysine residues of proteins in subjects diagnosed with RA are observed to be substituted with citrulline and homocitrulline, respectively, this substitution is not necessarily exhaustive. For example, a protein exhibiting citrulline substitutions in a subject with RA may still include one or more unsubstituted arginine residues. Accordingly, at least a portion of the derivative peptides included in the first array design can be considered synthetic peptides as defined herein.

Statistical analysis included the following: (1) linear model at an alpha of 0.05 after multiple-testing correction for the detection of differences between groups. A 2-fold threshold is used for differences between group means (2) a sliding-window Kolmogorov-Smirnov test is used for autoantibody detection with a sliding window size of 8 amino acids (3) 2 sample t-test for mutation detection and (4) random forest model for classifier generation. All statistical analyses were performed in the R statistical programming environment.

Figure 3:
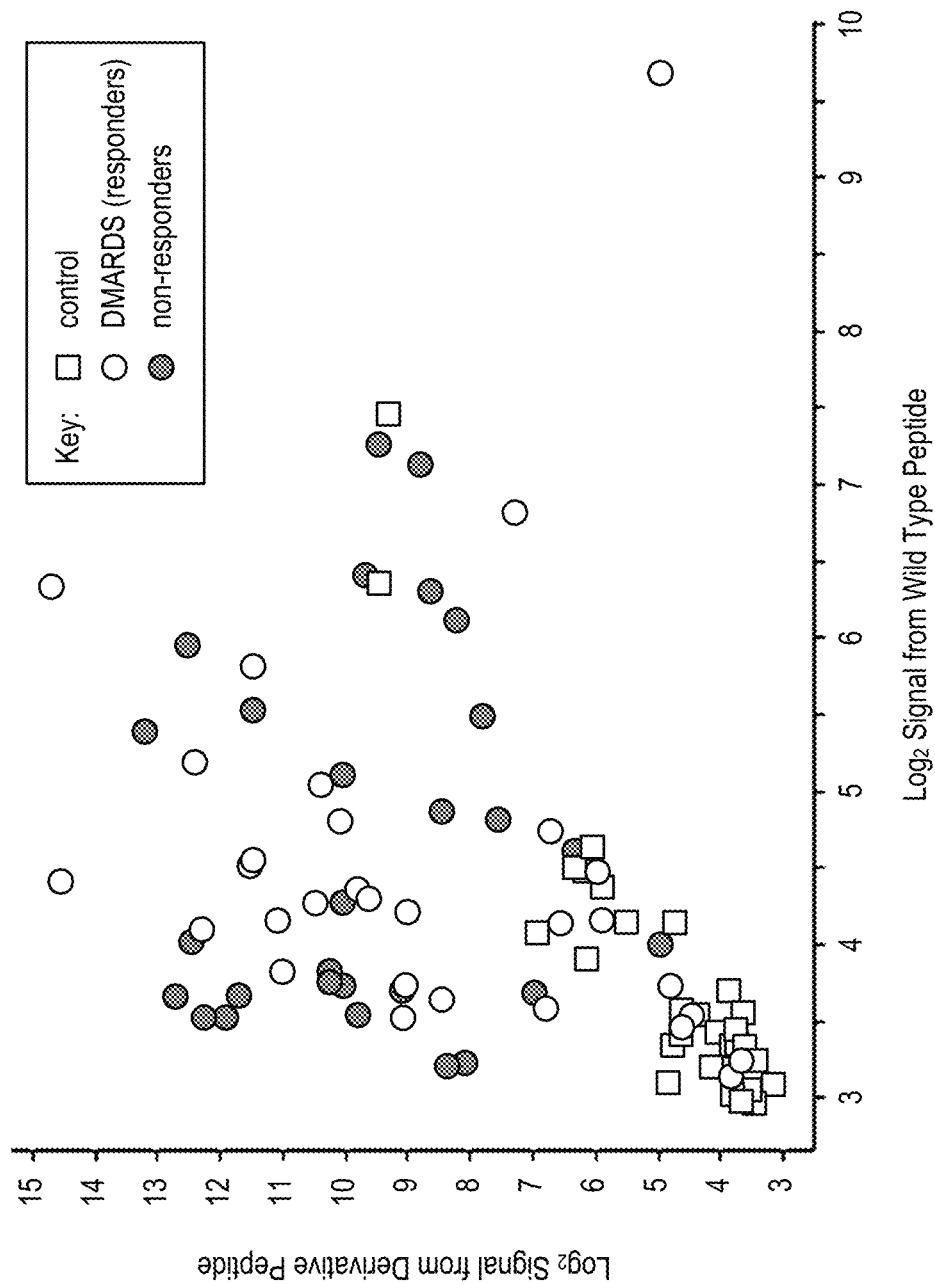
FIG. 3 is a scatter plot illustrating $\log_2$ signal output for a wild type peptide against the $\log_2$ signal output for a corresponding derivative of the wild-type peptide. The various groups are depicted according to their membership in the control group (empty squares) DMARDS/responders group (empty circles), or non-responders group (filled circles). Each data point represents a signal resulting from contacting different serum samples with the wild type and derivative peptides.

Referring to FIG. 3, statistical analysis revealed numerous peptides of the peptides present on the first array design that could sufficiently distinguish between the control samples and the RA samples (either DMARDS or non-responders or both). However, no peptides were found to distinguish between DMARDS and non-responders in a statistically significant way.

Figure 4B:
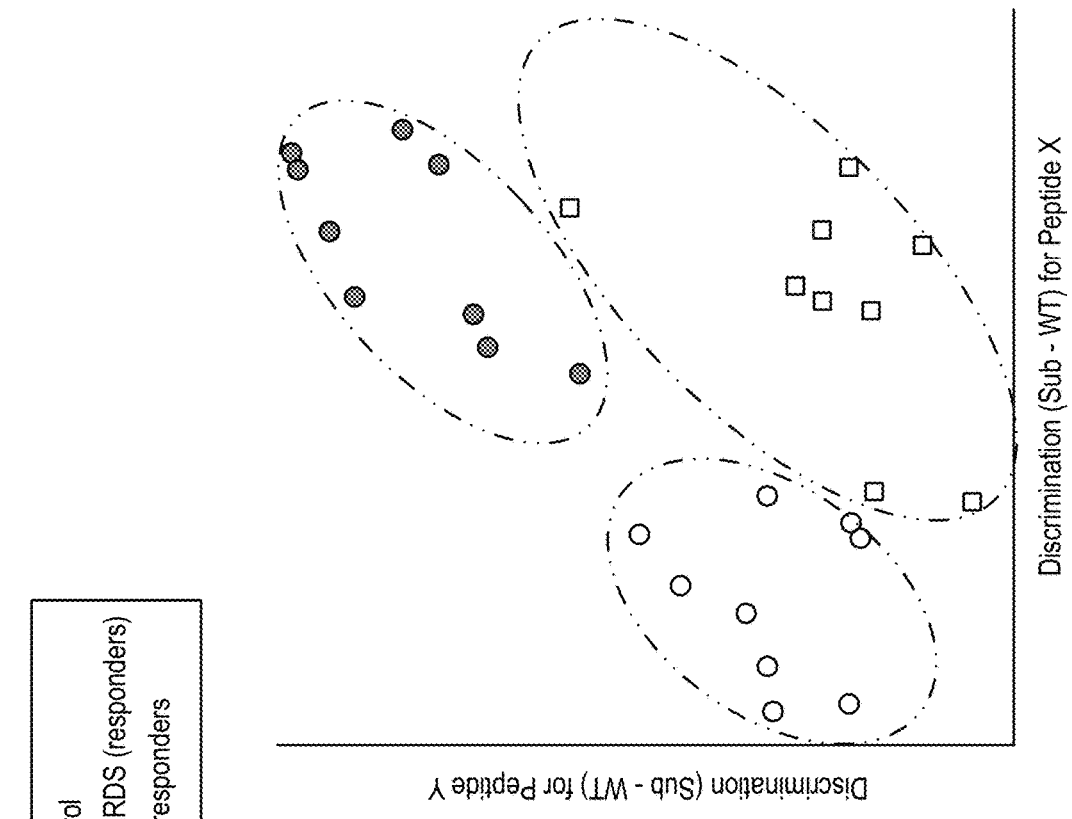
FIGS. 4A and 4B illustrate the development of a peptide classifier from wild-type and mutant peptides.
Figure 4A:
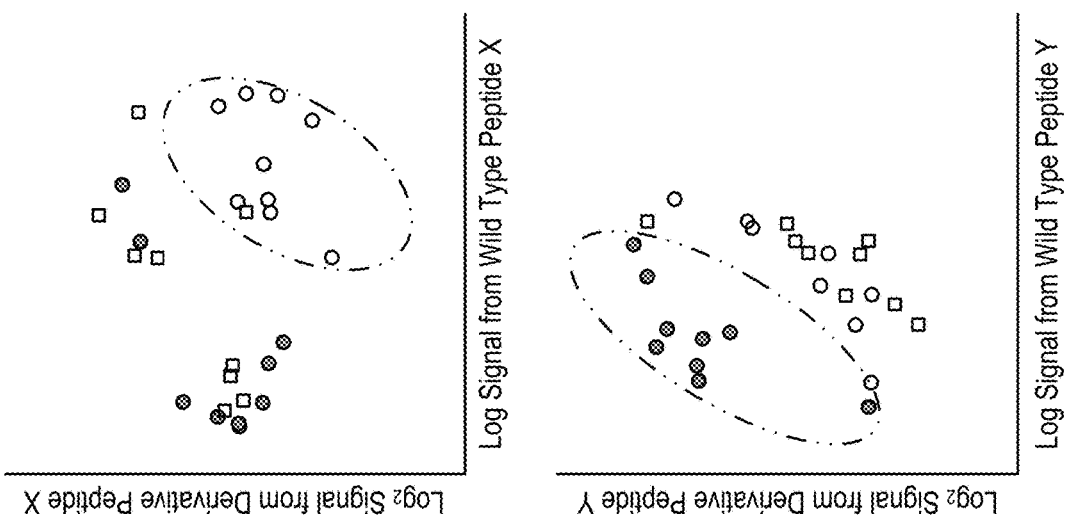

To assess whether there existed any peptide in the human proteome that can distinguish between the 3 groups: Controls, DMARDS and non-responders, a second array design was created that expanded upon the 52 proteins from the first array design to include the entire human proteome including both natural and derivative peptides synthesized by substituting citrulline and homo-citrulline for arginine and lysine, respectively. As discussed above, at least a portion of the derivative peptides included in the second array design can be considered synthetic peptides as defined herein. For the second array design, proteins were tiled with overlapping 12-mer to 16-mer peptides at 4 amino-acid tiling resolution (see FIG. 2 for an example of 4 amino-acid tiling resolution). For screening of the entire human proteome, a subset of ten (10) serum samples from each of the groups were selected and profiled with the second array design. Referring to FIG. 4A, statistical analyses revealed several peptides capable of distinguishing between the DMARDS and non-responders group. Notably, data is shown for only two of the peptides that were capable of distinguishing between the DMARDS and non-responders group. Upon inspection, by converting the $\log_2$ signal of these two peptides to the $\log_2$ signal difference between the derivative peptides and the wild-type counterpart, separation between the three groups (i.e., control, DMARDS, and non-responders) can be seen (FIG. 4B).

Figure 5:
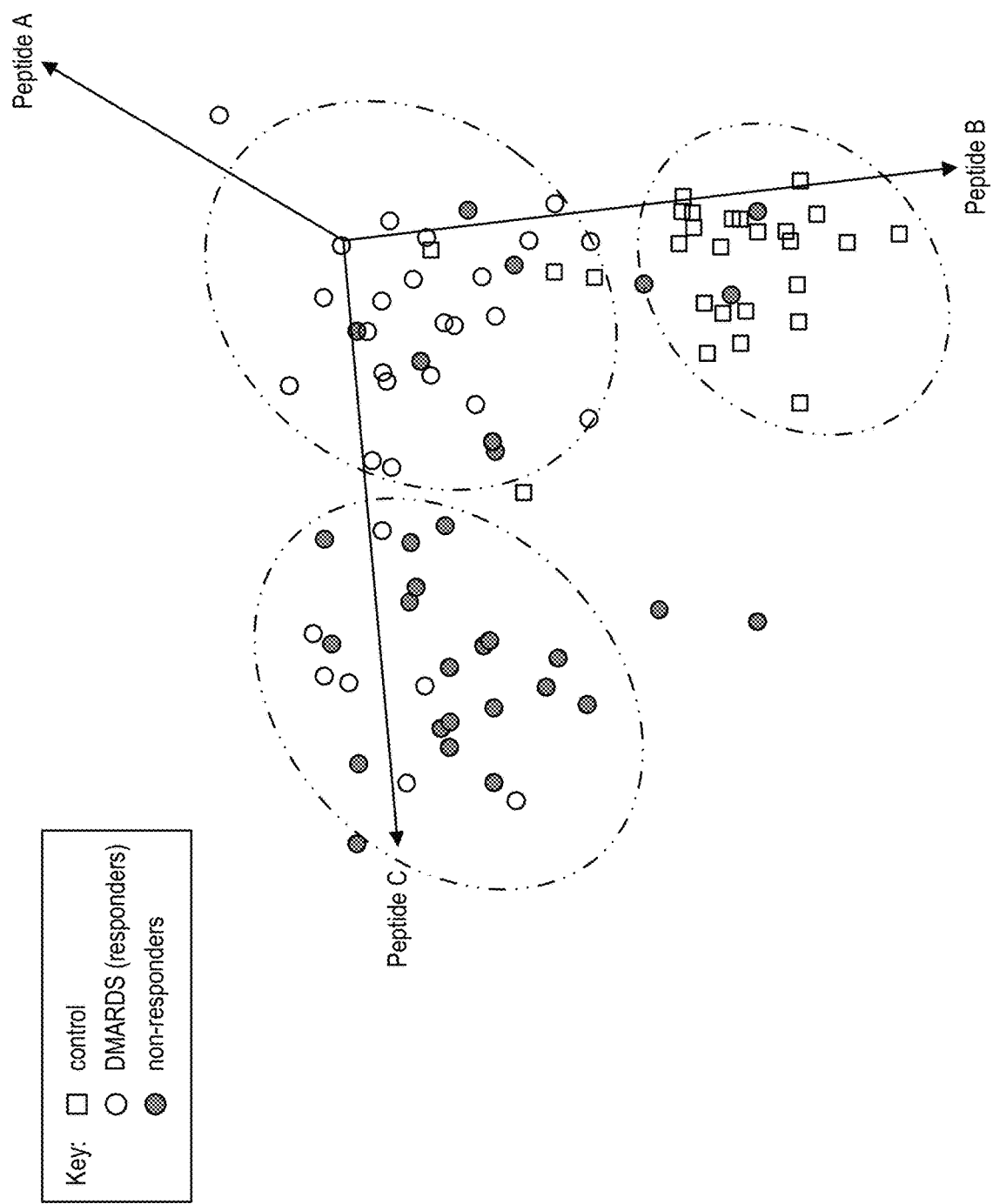
FIG. 5 is a signal plot generated for a 3-peptide synthetic classifier. Each data point represents a single serum sample depicted by their group membership in the control group (empty squares), DMARDS/responders group (empty circles), or non-responders group (filled circles). $\log_2$ signal response for serum samples in the presence of each of the three different peptides is shown on a respective one of the three different axes.
Figure 6:
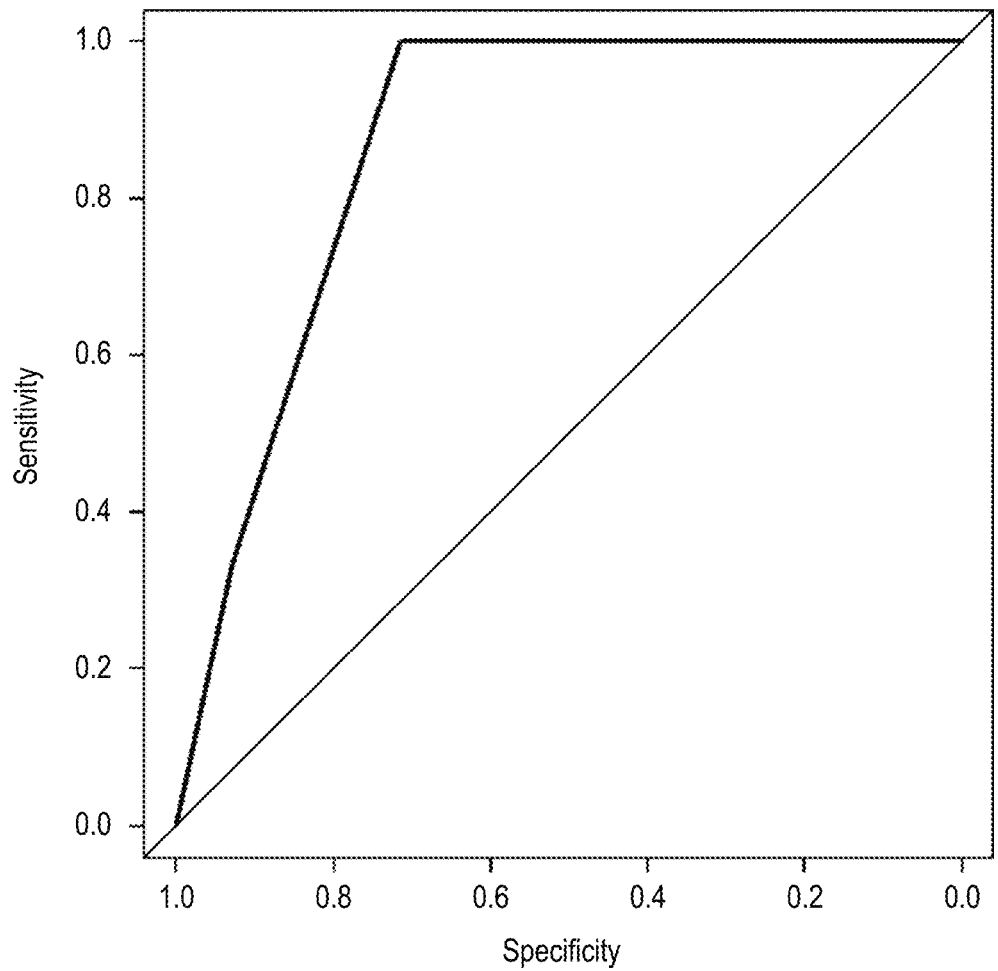
FIG. 6 is a plot showing the multiclass receiver operational characteristics (ROC) performance of a 3 peptide synthetic classifier according to the present disclosure. The plot illustrates the ability of the combination of 3 synthetic peptides to distinguish between the DMARDS/responders group and the non-responders group.
Figure 7:
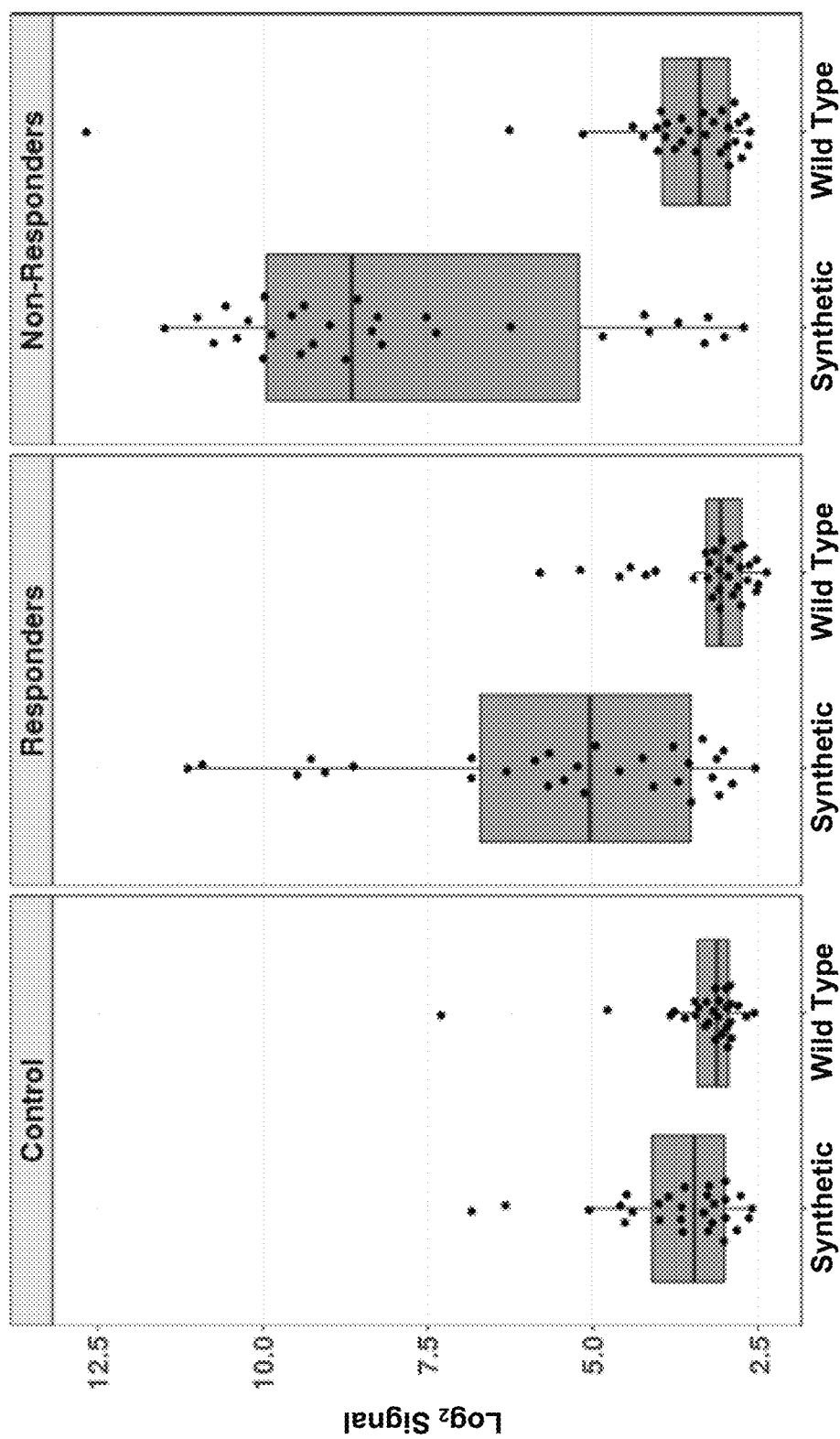
FIG. 7 is a box and whisker plot comparing the $\log_2$ signal response for synthetic peptide C from FIG. 5 with a corresponding wild-type peptide for each of three different sample cohorts. Each data point represents the signal measured from the interaction of either the synthetic peptide C or wild type peptide C with a given serum sample.

While it is possible that for certain biomarkers or disease types, a sufficient classifier could be prepared from naturally occurring peptides (i.e., the peptides included in the second array design), further improvements to the classifier performance were achieved with a third array design prepared by first selecting the top 97 candidate peptides based on their statistical significance and ability to distinguish between the three subject groups. Next, a number of variant peptide sequences were prepared by performing a systematic substitution analysis where every position of a candidate peptide is substituted (one at a time) with either one of the twenty natural amino acids, citrulline, or homocitrulline. Notably, substitution of an amino acid within a given candidate peptide sequence with citrulline or homocitrulline was performed agnostic of the original identity of the amino acid at that position. Therefore, as discussed above, at least a portion of the variant peptides included in the third array design can be considered synthetic peptides as defined herein. Using this new 12-plex design of greater than 34,144 variant peptides accounting for all single substitutions of the 97 candidate peptides, all 90 serum samples were profiled. Manual curation based on statistical analysis revealed a 3-peptide classifier that distinguished between all three groups with a multi-class receiver operational characteristics (ROC) performance of 0.86 (FIGS. 5-7). Each of the three synthetic peptides that made up the classifier included at least one modification relative to the corresponding wild-type (i.e., naturally occurring) peptide sequence. In one aspect, each of the three synthetic peptides included at least a substitution of an amino acid with citrulline or another canonical amino acid relative to the wild-type peptide counterpart.

Notably, the surprising discovery was made that three synthetic (i.e., non-naturally occurring) peptides selected from the variant peptides in the third array design could provide an equally good, if not a better classifier than any individual or combination of the naturally occurring (i.e., wild-type or mutant) peptides. In one aspect, FIG. 7 illustrates the impact of a synthetic peptide on measured signal relative to a corresponding wild-type peptide both for a given cohort and across cohorts. Importantly, this approach for designing synthetic peptides for querying biomarkers can be used in cases where initial classifier development with naturally occurring peptides (including wild-type peptides and known or expected mutants thereof) is not sufficient. That is, the present disclosure provides for an approach that can yield a more generalizable solution to biomarker detection and classification).

Example 2

Using a maskless array synthesis platform for the production of high-density peptide arrays, peptide classifier discovery, and subsequent enhancement via systematic amino acid substitution of lead peptides can be applied to generate a synthetic peptide classifier that distinguishes between healthy controls, diseased patients that respond to first line treatment, and diseased patients that are refractory to first line treatment.

In addition to autoimmune diseases such as RA (see Example 1), a similar methodology can be applied for the construct a classifier based on patient responsiveness to cancer immunotherapy. To that end, the serum samples of 45 cancer patients were profiled prior to undergoing immunotherapy. Of the 45 patients, 15 were eventually unresponsive to treatment (i.e., progressive disease), and 30 were at least partially responsive to treatment (i.e., complete response, partial response, and stable disease). Serum samples were comprehensively profiled on a pan-proteome peptide array that included the complete annotated human proteome tiled with overlapping 16 amino acid peptides with a 4 amino acid tiling resolution (see FIG. 2 for an example of 4 amino-acid tiling resolution). Using a random forest model for statistical analysis of the resulting data, specific peptides were selected from the tested peptides to minimize the group prediction error (i.e., the out-of-bag error). Using this approach an OOB error rate of less than 10% was achieved with a classifier composed of 5 or fewer naturally occurring peptides. Based on the specific lead wild type peptides identified, systematic substitution analysis can be performed to assess whether specific synthetic peptides will lead to a synthetic classifier that performs better than the previously identified classifier composed of naturally occurring peptides. If specific mutant peptides lead to better performing classifiers, it will serve to demonstrate the applicability of the methodology disclosed herein to patient stratification for cancer immunotherapy.

It will be appreciated, however, that the application of the disclosed classifier discovery and enhancement methodology is not limited to only RA and cancer. It is conceivable that the method of the present disclosure can be applied to any disease where antibody repertoire has a specific impact on either disease prognosis or disease etiology. Examples where antibody repertoire has been implicated in disease prognosis or disease etiology include, but are not limited to, other autoimmune diseases such as systemic lupus erythematosus (SLE) and inflammatory bowel disease (IBD), and host-vs.-graft diseases during transplantation.

The schematic flow charts shown in the Figures are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the Figures are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention. Accordingly, the foregoing description is meant to be exemplary, and does not limit the scope of present inventive concepts.

Each reference identified in the present application is herein incorporated by reference in its entirety.

What is claimed is:

1. A method for identifying a synthetic classifier, the method comprising:
   contacting at least a first sample and a second sample with a first plurality of peptides, wherein:
   the first sample derived from a first group of a cohort,
   the second sample derived from a second group of the cohort,
   the first group being different from the second group, and
   the first plurality of peptides including:
   i) a first subset of peptides defining at least one naturally occurring amino acid sequence, and
   ii) a second subset of peptides defining a plurality of variant peptides of the first subset of peptides, the plurality of variant peptides including for each one of the first subset of peptides, a variant peptide having at least one of a substitution, a deletion, an insertion, an extension, and a modification relative to a corresponding one of the first subset of peptides, wherein each of the variant peptides is a synthetic peptide;
   selecting at least one of the plurality of variant peptides from the second subset of peptides; and
   defining a synthetic classifier including the at least one of the plurality of variant peptides, the synthetic classifier distinguishing between a sample derived from the first group and a sample derived from the second group.

2. The method of claim 1, wherein at least a portion of the first plurality of peptides represents at least 90%±10% of a target proteome, the target proteome selected from a virus and an organism.

3. The method of claim 1, wherein the synthetic classifier distinguishes between the sample derived from the first group and the sample derived from the second group with at least one of a greater sensitivity and a greater specificity than a natural classifier consisting of peptides selected from the first subset of peptides.

4. The method of claim 1, wherein each of the peptides in the first plurality of peptides is between 12 amino acids and 16 amino acids in length.

5. The method of claim 1, wherein the peptides in the first plurality of peptides are tiled at between 1 amino acid and 4 amino acids.

6. The method of claim 1, wherein each one of the variant peptides corresponds to a naturally occurring peptide, and wherein each one of the variant peptides has a sequence that differs from the corresponding naturally occurring peptides sequence with respect to at least one amino acid position.

7. The method of claim 1, wherein the at least one of the plurality of variant peptides in the synthetic classifier is a synthetic peptide having a sequence that differs from any naturally occurring peptide sequence associated with either of the first group and the second group.

8. The method of claim 1, wherein prior to the selecting at least one of the plurality of variant peptides from the second subset of peptides the method further comprises:
   detecting a first signal output characteristic of an interaction of each of the first sample and the second sample with the first plurality of peptides;
   selecting the first subset of peptides based on the first signal output; and
   detecting a second signal output characteristic of an interaction of each of the first sample and the second sample with the second subset of peptides, wherein the selecting at least one of the plurality of variant peptides from the second subset of peptides is based on the second signal output.

9. The method of claim 8, wherein the first signal output is a fluorescence intensity obtained through fluorophore excitation-emission, the fluorescence intensity reflecting at least one of i) an abundance of a component of one of the first sample and the second sample associated with the first plurality of peptides, and ii) a binding affinity of the component of one of the first sample and the second sample to the first plurality of peptides.

* * * * *